United States Patent

Some

Patent Number: 6,064,755
Date of Patent: May 16, 2000

[54] IMAGE ANALYZING APPARATUS FOR PRODUCING DENSITY PROFILE DATA OF AN IMAGE

[75] Inventor: Masato Some, Kanagawa-Ken, Japan

[73] Assignee: Fuji Photo Film Co., Ltd., Kanagawa-Ken, Japan

[21] Appl. No.: 08/883,429

[22] Filed: Jun. 26, 1997

[30] Foreign Application Priority Data

Jul. 5, 1996 [JP] Japan .................................... 8-176372

[51] Int. Cl.[7] .................................................. G06K 9/00
[52] U.S. Cl. ............................ 382/132; 382/168; 382/170
[58] Field of Search ..................................... 382/128, 132, 382/134, 168, 172, 170, 254, 275

[56] References Cited

U.S. PATENT DOCUMENTS

| | | | |
|---|---|---|---|
| 5,028,793 | 7/1991 | Lindmayer et al. | 250/484.1 |
| 5,369,572 | 11/1994 | Haraki et al. | 382/132 |
| 5,644,388 | 7/1997 | Maekawa et al. | 382/134 |

FOREIGN PATENT DOCUMENTS

| | | | |
|---|---|---|---|
| 59-15843 | 1/1984 | Japan | G01N 23/20 |
| 61-51738 | 3/1986 | Japan | H01J 37/22 |
| 61-93538 | 5/1986 | Japan | H01J 37/20 |
| 1-60782 | 12/1989 | Japan | G01N 33/58 |
| 1-60784 | 12/1989 | Japan | G01N 33/60 |
| 4-3952 | 1/1992 | Japan | C12N 15/00 |
| 2 246 197 | 1/1992 | United Kingdom | G01N 21/76 |

*Primary Examiner*—Matthew C. Bella
*Attorney, Agent, or Firm*—Sughrue, Mion, Zinn, Macpeak & Seas, PLLC

[57] ABSTRACT

An image analyzing apparatus for, producing a profile of density of a predetermined image region to display it on a CRT and effecting quantitative analysis. The image analyzing apparatus includes a profile data producing section for producing profile data of density of a predetermined image region, a background noise level calculating section for defining a region of interest in the profile displayed on the CRT based on the profile data produced by the profile data producing section and calculating the average value of density levels of pixels of image data corresponding to an image in the defined region of interest as a background noise level, and a profile data correcting section for subtracting the background noise level produced by the background noise level calculating section from the profile data produced by the profile data producing section to correct the profile data.

22 Claims, 5 Drawing Sheets

IMAGE ANALYZING APPARATUS FOR PRODUCING DENSITY PROFILE DATA OF AN IMAGE

BACKGROUND OF THE INVENTION

The present invention relates to an image analyzing apparatus and, particularly, to such an apparatus which can produce a density profile of an image region in a gray image in a desired manner and analyze images.

DESCRIPTION OF THE PRIOR ART

Various image analyzing methods are known. These include an autoradiographic process comprising the steps of introducing a radioactively labeled substance into an organism, using the organism or a part of the tissue of the organism as a specimen, placing the specimen and a radiographic film such as a high sensitivity type X-ray film together in layers for a certain period of time to expose the radiographic film thereto and obtaining locational information on the radioactively labeled substance in the specimen from the resolved pattern of the radiographic film, a chemiluminescent process comprising the steps of selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, detecting the chemiluminescent emission in the wavelength of visible light generated by the contact of the chemiluminescent substance and the labeling substance and obtaining information relating to the high molecular substance such as genetic information, a detecting method using an electron microscope comprising the steps of irradiating a metal or nonmetal specimen with an electron beam, detecting a diffraction image, transmission image or the like and effecting elemental analysis, composition analysis of the specimen, structural analysis of the specimen or the like, or irradiating the tissue of an organism with an electron beam and detecting an image of the tissue of the organism, and a radiographic diffraction image detecting process comprising the steps of irradiating a specimen with radiation, detecting a radiographic diffraction image and effecting structural analysis of the specimen or the like.

Conventionally, these methods are carried out by employing a photographic film as a detecting material, recording a radiographic image, a chemiluminescent image, an electron microscopic image, a radiographic diffraction image or the like on the photographic film and observing a visual image with the eyes. However, in the case where a photographic film is employed as a detecting material, since a radiographic film has low sensitivity, there is a problem that it takes considerable time for recording an image in the autoradiographic process and the radiographic diffraction image detecting process. Further, in the chemiluminescent process, although it is necessary to employ a highly sensitive film having a high gamma value for detecting very weak chemiluminescent emission, when the highly sensitive film having a high gamma value is employed, it is difficult to expose the film reliably using a straight portion of the characteristic curve. Therefore, the film is often exposed improperly and it is necessary to repeatedly expose the films under various exposure conditions. Moreover, in the detecting process using the electron microscope, since the straight portion of the characteristic curve of a photo-graphic film for an electron microscope is short, it is difficult to determine the proper exposure condition and it is necessary to repeatedly expose the films. Furthermore, in either processes, it is indispensable to chemically develop the films and, therefore, the operations are unavoidably complicated.

In view of the above, there have been proposed an autoradiographic process, a chemiluminescent process, a detecting process using an electron so microscope and a radiographic diffraction image detecting process comprising the steps of employing, as a detecting material for the radiation, the visible light, the electron beam or the like, not a photographic film, but a stimulable phosphor which can absorb and store the energy of radiation, visible light, an electron beam or the like upon being irradiated therewith and release a stimulated emission whose amount is proportional to that of the received radiation, the visible light, the electron beam or the like upon being stimulated with an electromagnetic wave having a specific wavelength range, photoelectrically detecting the stimulated emission released from the stimulable phosphor, converting the detection signal to a digital signal, effecting a predetermined image processing on the obtained image data and reproducing an image on displaying means such as a CRT or the like or a photographic film (See for example, Japanese Patent Publication No. 1-60784, Japanese Patent Publication No. 1-60782, Japanese Patent Publication No. 4-3952, U.S. Pat. No. 5,028,793, UK Patent Application 2,246,197 A, Japanese Patent Application Laid Open No. 61-51738, Japanese Patent Application Laid Open No. 61-93538, Japanese Patent Application Laid Open No. 59-15843 and the like).

According to the detecting processes using the stimulable phosphor, development, which is a chemical processing, becomes unnecessary. In addition, the exposure time can be markedly shortened in the autoradiographic process and the radiographic diffraction image detecting process. Improper exposure becomes rare and the exposing operation becomes easy in the chemiluminescent process and the detecting process using the electron microscope. Further, since the image is reproduced after the detected signal has been converted to a digital signal, the image can be reproduced in a desired manner by effecting signal processing on image data and it is also possible to effect quantitative analysis using a computer. Use of a stimulable phosphor in these process is therefore advantageous.

For effecting quantitative analysis, it is sometimes required to produce a density profile of an image region in a gray image and display it on a display means such as the screen of a CRT.

For example, the base sequence of DNA is determined by means of electrophoresis in accordance with the steps of dropping a plurality of specimens containing DNA fragments containing a specific gene onto a gel support medium at constant intervals, separating and distributing them by means of electrophoresis, denaturing them by alkali processing to form single-stranded DNA, fixing the denatured DNA fragments onto a filter according to the known Southern blot hybridization method, hybridizing them with labeled DNA or RNA which is complementary to the DNA containing the specific gene to label the DNA fragments containing the specific gene and imaging the distribution of a labeling substance. In this case, the lower the molecular weight of DNA is, the longer distance it travels. The image corresponding to the respective specimens are therefore distributed one-dimensionally, namely, lane-like and, therefore, the image obtained by electrophoresis includes a plurality of lane-like images equally spaced and parallel to each other. It is often required to produce a density profile of lane-like image regions in the thus obtained image for determining the base sequence of DNA by means of electrophoresis.

Further, in the thin layer chromatography (TLC) widely used in research into drug metabolism, how a drug labeled with a labeling substance and introduced into a test animal changes in the body of the animal is analyzed by collecting specimens of urine, blood, tissue or the like from a specific region of the animal at predetermined time intervals, processing the specimens in a predetermined manner and dropping the processed specimens at predetermined positions at regular intervals on a TLC plate which is formed by coating a glass plate with powders of silica gel. The TLC plate is dipped in a distribution solvent and the specimens are chromatographically distributed, thereby forming separate spots for individual components of the specimens. As a result, the specimens collected at predetermined time intervals are distributed one-dimensionally, namely, lane-like. A so-obtained image therefore includes a plurality of lane-like images equally spaced and parallel to each other. In this case, it is often required for determining how the drug was metabolized to produce a density profile of lane-like image regions in the thus obtained image.

Furthermore, in the case where a diffraction image or transmission image of a metal or nonmetal specimen is produced using an electron microscope and structural analysis of the specimen is effected or where an electron microscope image of the tissue of the organism is produced for observing the tissue of the organism, it is often required to specify a particular image region in the image and produce a density profile thereof.

However, in images produced by the thin layer chromatography (TLC) of protein or images produced for obtaining locational information regarding a gene, noise having a constant level is often generated in the background of the image reproduced on a display means because the stimulable phosphor sheet is uniformly exposed to ambient radiation or the like. Therefore, if a particular image region is specified and a density profile of the image region is merely produced, the density profile inevitably contains the background noise and quantitative analysis of the image cannot be effected based on the thus produced a density profile.

Therefore, conventionally, an operator views a profile displayed on a display means, specifies a density level thought to correspond to the density level of the background noise and subtracts the thus specified density level from the density profile, or an image processing apparatus automatically determines the lowest level among the density levels of image data to be the density level of the background noise and subtracts the thus determined density level from the density profile, thereby producing the density profile of the image region and effecting analysis based thereon.

However, it is not only very troublesome for the operator to view the profile displayed on the display means and to determine the density level of the background noise but also impossible to correctly determine the density level of the background noise unless the operator is skilled, thereby lowering the accuracy for analyzing images.

Further, it is not certain that the lowest level among the density levels of image data corresponds to the density level of the background noise but it is rather normal that the density level of the background noise is higher than the lowest level. Therefore, in the case where the image processing apparatus automatically determines the lowest level among the density levels of image data to be the density level of the background noise and subtracts the thus determined density level from the density profile, thereby producing the density profile of the image region, the accuracy for analyzing images is somewhat lowered.

The same problems occur in the case where, after an autoradiographic image, a chemiluminescent image, an electron microscopic image, a radiographic diffraction image or the like was recorded on a photographic film, the recorded image is photoelectrically read and converted to a digital signal and the thus obtained image signal is signal processed in a desired manner, thereby reproducing a visible image on displaying means such as a CRT or the like or a photographic film.

SUMMARY OF THE INVENTION

It is therefore an object of the present invention to provide an image analyzing apparatus which can produce a density profile of an image region in a gray image in a desired manner and analyze images.

The above and other objects of the present invention can be accomplished by an image analyzing apparatus comprising image data storing means for storing image data, image data memory means for two-dimensionally mapping and temporarily storing at least a part of the image data stored in the image data storing means and adapted for displaying an image on display means based on the image data temporarily stored in the image data memory means, producing a profile of density of a predetermined image region to display it on the display means and effecting quantitative analysis, the image analyzing apparatus further comprising profile data producing means for producing profile data of density of a predetermined image region and storing them in the image data memory means, background noise level calculating means for defining a region of interest in the profile displayed on the display means based on the profile data produced by the profile data producing means 5 and calculating an average value of density levels of pixels of image data corresponding to an image in the defined region of interest as a background noise level and profile data correcting means for subtracting the background noise level produced by the background noise level calculating means from the profile data produced by the profile data producing means to correct the profile data and storing the corrected profile data in the image data memory means, the display means being adapted to display the profile data stored in the image data memory means.

In a preferred aspect of the present invention, the background noise level calculating means is constituted so as to output the calculated background noise level to the image data memory means and the display means is constituted so as to synthesize the profile data produced by the profile data producing means and stored in the image data memory means and the background noise level calculated by the background noise level calculating means and stored in the image data memory means and display them.

In a further preferred aspect of the present invention, the image data are produced using a stimulable phosphor sheet.

In a further preferred aspect of the present invention, the image data are constituted by image data selected from a group consisting of autoradiographic image data, radiographic diffraction image data, electron microscopic image data and chemiluminescent image data.

In a still further preferred aspect of the present invention, the autoradiographic image data, the radiographic diffraction image data and the electron microscopic image data are produced by absorbing and storing the energy of a radiation or an electron beam emitted from a specimen in a stimulable phosphor, irradiating the stimulable phosphor with an electromagnetic wave and photoelectrically converting light emitted from the stimulable phosphor.

In a further preferred aspect of the present invention, the chemiluminescent image data are produced by absorbing and storing the energy of a visible light emitted from a specimen in a stimulable phosphor, irradiating the stimulable phosphor with an electromagnetic wave and photoelectrically converting light emitted from the stimulable phosphor.

In the present invention, the stimulable phosphor employed for producing an autoradiographic image, a radiographic diffraction image and an electron microscopic image may be of any type insofar as it can store radiation energy or electron beam energy and can be stimulated by an electromagnetic wave to release the radiation energy or electron beam energy stored therein in the form of light. However, a stimulable phosphor which can be stimulated by light having a visible light wavelength is preferably employed. More specifically, preferably employed stimulable phosphors include alkaline earth metal fluorohalide phosphors $(Ba_{1-x}, M^{2+}{}_x)FX:yA$ (where $M^{2+}$ is at least one alkaline earth metal selected from the group consisting of Mg, Ca, Sr, Zn and Cd; X is at least one halogen selected from the group consisting of Cl, Br and I, A is at least one element selected from the group consisting of Eu, Tb, Ce, Tm, Dy, Pr, He, Nd, Yb and Er; x is equal to or greater than 0 and equal to or less than 0.6 and y is equal to or greater than 0 and equal to or less than 0.2.) disclosed in U.S. Pat. No. 4,239,968, alkaline earth metal fluorohalide phosphors SrFX:Z (where X is at least one halogen selected from the group consisting of Cl, Br and I; and Z is at least one of Eu and Ce.) disclosed in Japanese Patent Application Laid Open No. 2-276997, europium activated complex halide phosphors $BaFX \cdot xNaX':aEu^{2+}$ (where each of X or X' is at least one halogen selected from the group consisting of Cl, Br and I; x is greater than 0 and equal to or less than 2; and y is greater than 0 and equal to or less than 0.2.) disclosed in Japanese Patent Application Laid Open No. 589-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1.) disclosed in Japanese Patent Application Laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br, and I; and x is greater than 0 and equal to or less than 0.1.) disclosed in U.S. Pat. No. 4,539,137 and europium activated complex halide phosphors $M''FX \cdot aM'X' \cdot bM'''X''_2 \cdot cM'''X'''_3 \cdot xA:yEu^{2+}$ (where M'' is at least one alkaline earth metal selected from the group consisting of Ba, Sr and Ca; M' is at least one alkaline metal selected from the group consisting of Li, Na, K, Rb and Cs; M''' is at least one divalent metal selected from the group consisting of Be and Mg; M'''' is at least one trivalent metal selected from the group consisting of Al, Ga, In and Tl; A is at least one metal oxide; X is at least one halogen selected from the group consisting of Cl, Br and I; each of X', X'' and X''' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2.) disclosed in U.S. Pat. No. 4,962,047.

In the present invention, the stimulable phosphoremployed for producing a chemiluminescent image may be of any type insofar as it can store the energy of light having a visible light wavelength and can be stimulated by an electromagnetic wave to release the energy of light having a visible light wavelength stored therein in the form of light. However, a stimulable phosphor which can be stimulated by light having a visible light wavelength is preferably employed. More specifically, preferably employed stimulable phosphors include metal halophosphates, rare-earth-activated phosphors, aluminate-host phosphors, silicate-host phosphors and fluoride-host phosphors disclosed in UK Patent Application 2,246,197 A.

The above and other objects and features of the present invention will become apparent from the following description made with reference to the accompanying drawings.

DESCRIPTION OF THE PREFERRED EMBODIMENT

Figure 1:
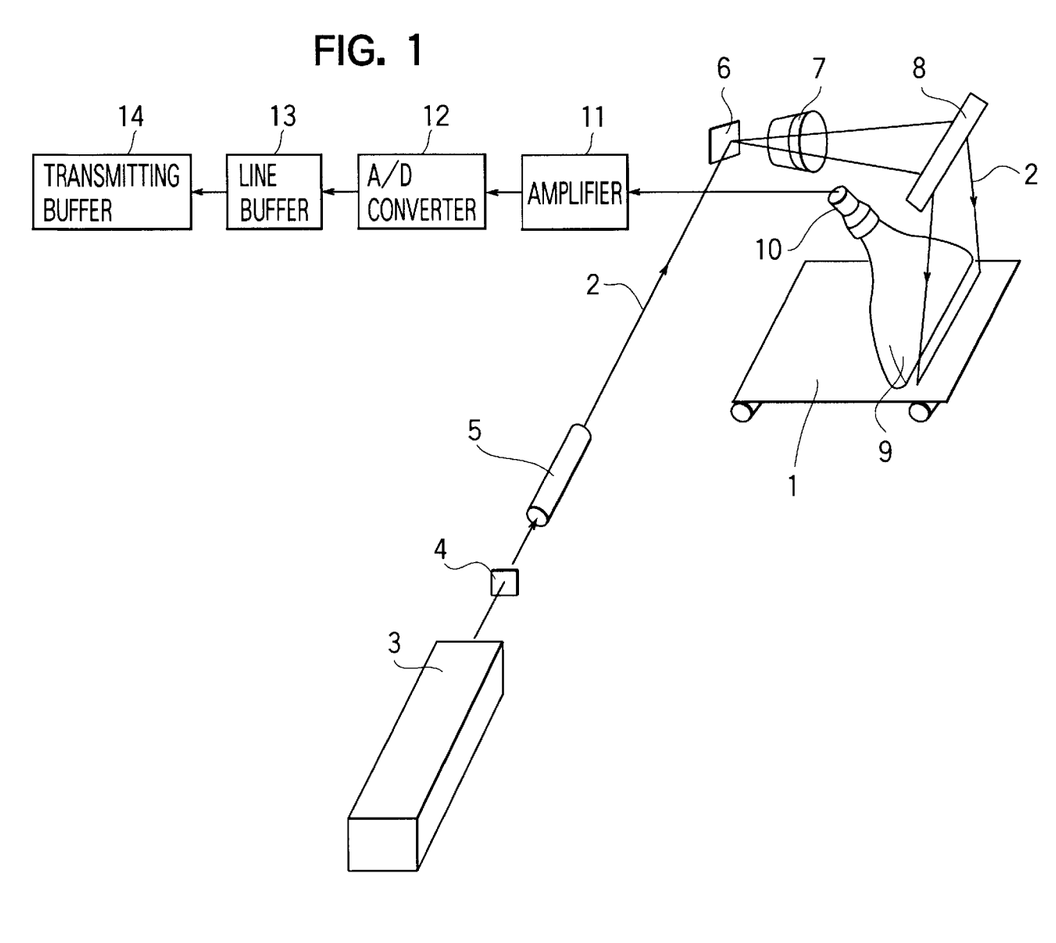
FIG. 1 is a schematic perspective view showing an image reading apparatus for producing image data to be analyzed by an autoradiographic image analyzing apparatus which is an embodiment of the present invention.

A stimulable phosphor sheet 1 shown in FIG. 1 stores locational information regarding radioactive labeling material contained in a specimen (not shown) in the form of radioactive energy. Locational information as termed here includes a variety of information relating to the location of radioactive labeled substances, or aggregations thereof, present in a specimen, such as the location, the shape, the concentration, the distribution or combinations thereof.

In this embodiment, the stimulable phosphor sheet 1 stores an autoradiographic image of a radioactively labeled substance contained in a gene produced by the Southern blot hybridization method.

The stimulable phosphor sheet which stores the locational information regarding a radioactive material in the specimen in this manner is scanned with a laser beam 2 and stimulated, thereby being caused to emit stimulated emission.

The laser beam 2 is generated by a laser beam source 3 and passes through a filter 4 to cut off light in the wavelength region corresponding to the wavelength region of stimulated emission to be emitted from the stimulable phosphor sheet 1 in response to stimulation by the laser beam 2. The beam diameter of the laser beam 2 is accurately adjusted by a beam expander 5 and the laser beam 2 enters a beam deflector 6 such as a galvanometer. The laser beam 2 deflected by the beam deflector 6 passes through an f lens 7 and is reflected by a plane reflecting mirror 8, thereby impinging upon the stimulable phosphor sheet 1. The f lens 7 ensures that the stimulable phosphor sheet 1 is always scanned with the laser beam 2 at a uniform beam speed.

Figure 4:
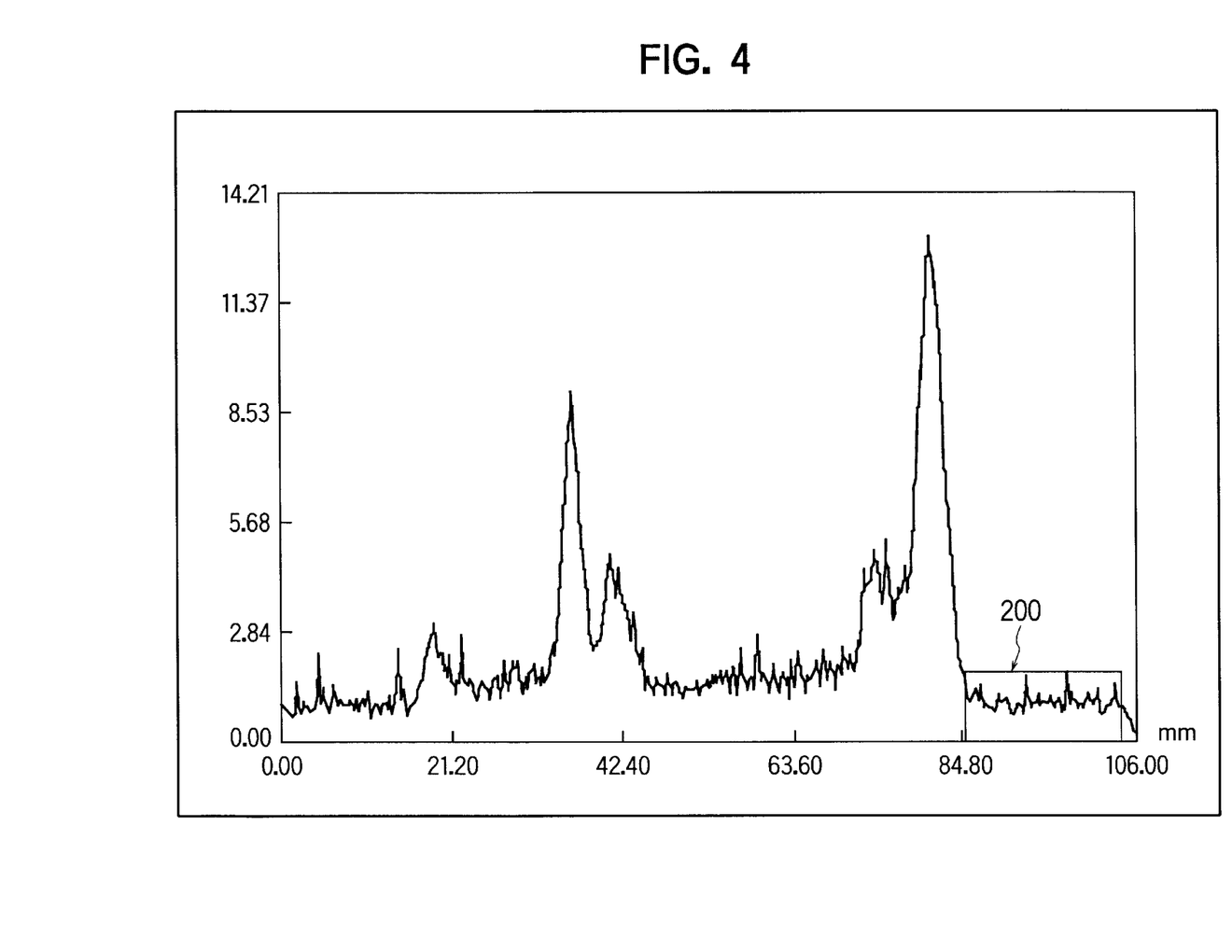
FIG. 4 shows a screen of CRT in which a region of interest is defined in a density profile.

The stimulable phosphor sheet 1 is conveyed in the direction along the arrow in FIG. 4 in synchronism with the above mentioned scanning with the laser beam 2 so that the whole surface of the stimulable phosphor sheet 1 is scanned by the laser beam 2.

When irradiated with the laser beam 2, the stimulable phosphor sheet 1 releases stimulated emission in an amount proportional to the radiation energy stored therein and the stimulated emission enters a light guiding sheet 9.

The light receiving end of the light guiding sheet 9 has a linear shape and is positioned in the vicinity of the stimulable phosphor sheet 1 so as to face the scanning line on the stimulable phosphor sheet 1. The exit end of the light guiding sheet 9 is in the form of a ring and is connected to the light receiving surface of a light detector 10 such as a photomultiplier for photoelectrically detecting light. This light guiding sheet 9 is made by processing a transparent thermoplastic resin sheet such as an acrylic synthetic resin and so constituted that the emission introduced from the light receiving end is transmitted to the exit end under repeated total reflection within the light guiding sheet 9 and received by the light receiving surface of the light detector 10 via the exit end.

Therefore, the stimulated emission produced by the stimulable phosphor sheet 1 upon being irradiated with the laser beam 2 enters into the light guiding sheet 9 and is received by the light detector 10 via the exit end under repeated total reflection within the sheet 9.

On the light receiving surface of the light detector 10 is provided a filter which allows only light of the wavelength region of the stimulated emission released from the stimulable phosphor sheet 1 to pass through and cuts off light of the wavelength region of the laser beam so that the light detector 10 can photoelectrically detect only the stimulated emission released from the stimulable phosphor sheet 1.

The stimulated emission photoelectrically detected by the light detector 10 is converted to an electrical signal, amplified by an amplifier 11 having a predetermined amplifying factor so as to produce an electrical signal of a predetermined level and then input to an AND converter 12. The electrical signal is converted to a digital signal with a scale factor suitable for the signal fluctuation width and input to a line buffer 13. The line buffer 13 temporarily stores image data corresponding to one scanning line. When the image data corresponding to one scanning line have been stored in the line buffer 13 in the above described manner, the line buffer 13 outputs the data to a transmitting buffer 14 whose capacity is greater than that of the line buffer 13 and when the transmitting buffer 14 has stored a predetermined amount of the image data, it outputs the image data to an autoradiographic image forming apparatus.

Figure 2:
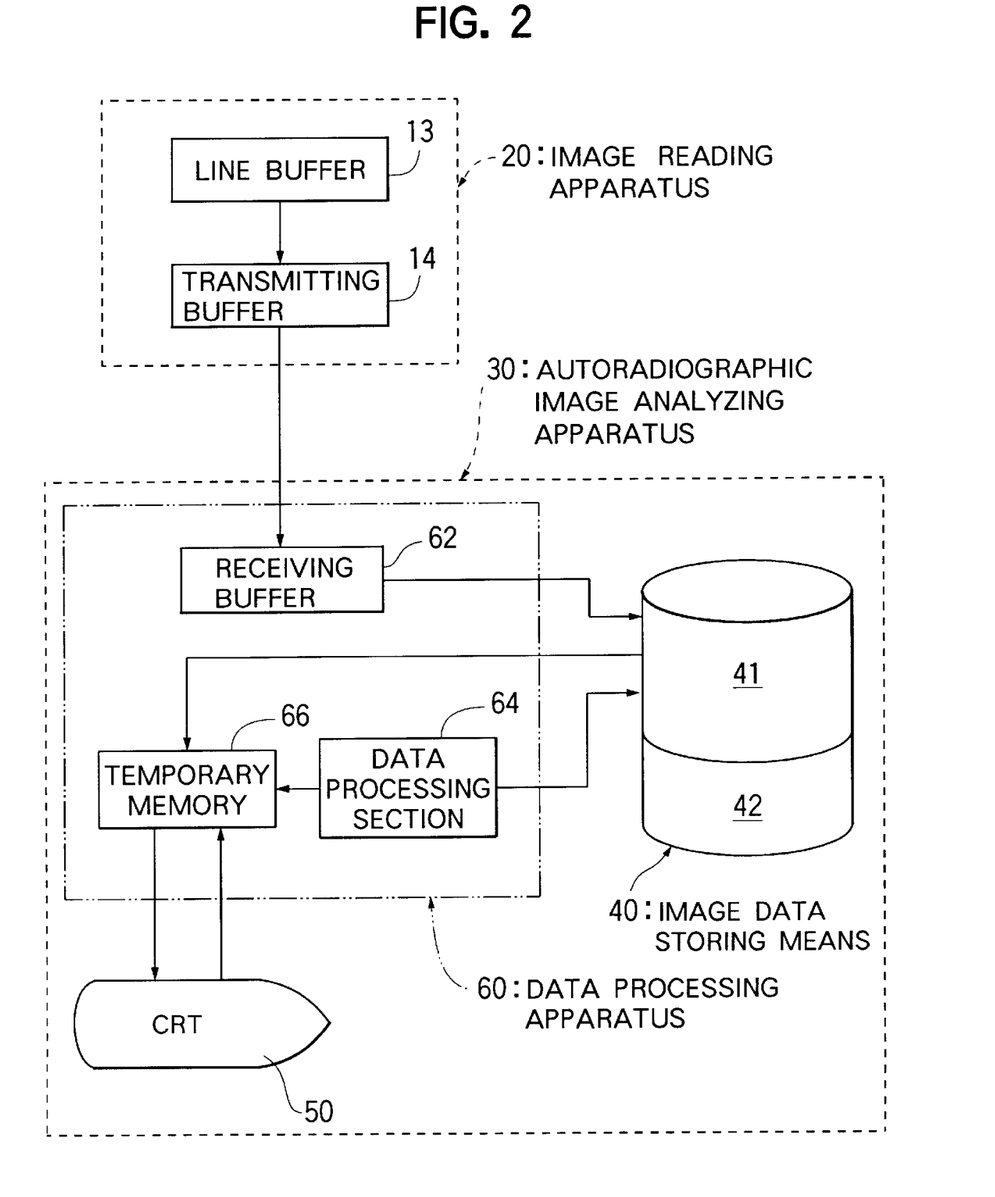
FIG. 2 is a block diagram of an autoradiographic image analyzing apparatus and an image reading apparatus.

FIG. 2 is a block diagram of the autoradiographic image analyzing apparatus and an image reading apparatus.

As shown in FIG. 2, the autoradiographic image analyzing apparatus 30 includes data processing means 60 for receiving image data containing locational information regarding a radioactive labeled substance contained in a specimen, which were stored and recorded in the stimulable phosphor sheet 1, read out by the image reading apparatus 20 and converted to a digital signal, and processing them so as to reproduce a visible image which has desirable density, tone, contrast and the like, and has excellent observation and analysis property, image data storing means 40 for storing image data which were input to the data processing means 60 from the image reading apparatus 20 and processed thereby, and a CRT 50 for reproducing an image based on the image data containing locational information regarding a radioactive labeled substance contained in a specimen.

The image data temporarily stored in the transmitting buffer 14 of the image reading apparatus 20 are input to a receiving buffer 62 in the data processing means 60 of the autoradiographic image analyzing apparatus 30 and temporarily stored therein. When a predetermined amount of the image data have been stored, the stored image data are output to an image data temporary storing section 41 in the image data storing means 40 and stored therein. In this manner, the image data fed from the transmitting buffer 14 of the image reading apparatus 20 to the receiving buffer 62 of the data processing means 60 and temporarily stored therein are fed from the transmitting buffer 14 to the image data temporary storing section 41 in the image data storing means 40. When the image data obtained by scanning the whole surface of the stimulable phosphor sheet 1 with the laser beam 2 have been stored in the image data temporary storing section 41 in the image data storing means 40, the data processing section 64 in the data processing means 60 reads the image data from the image data temporary storing section 41 and stores them in a temporary memory 66 in the data processing means 60. After the image data were subjected to necessary data processing in the data processing section 64, the data processing section 64 stores only the processed image data in an image data storing section 42 in the image data storing means 40. The data processing section 64 then erases the image data stored in the image data temporary storing section 41.

The image data stored in the image data storing section 42 in the image data storing means 40 can be read by the data processing section 64 and displayed on the screen of the CRT 50 so that an operator can view and analyze the image.

Figure 3:
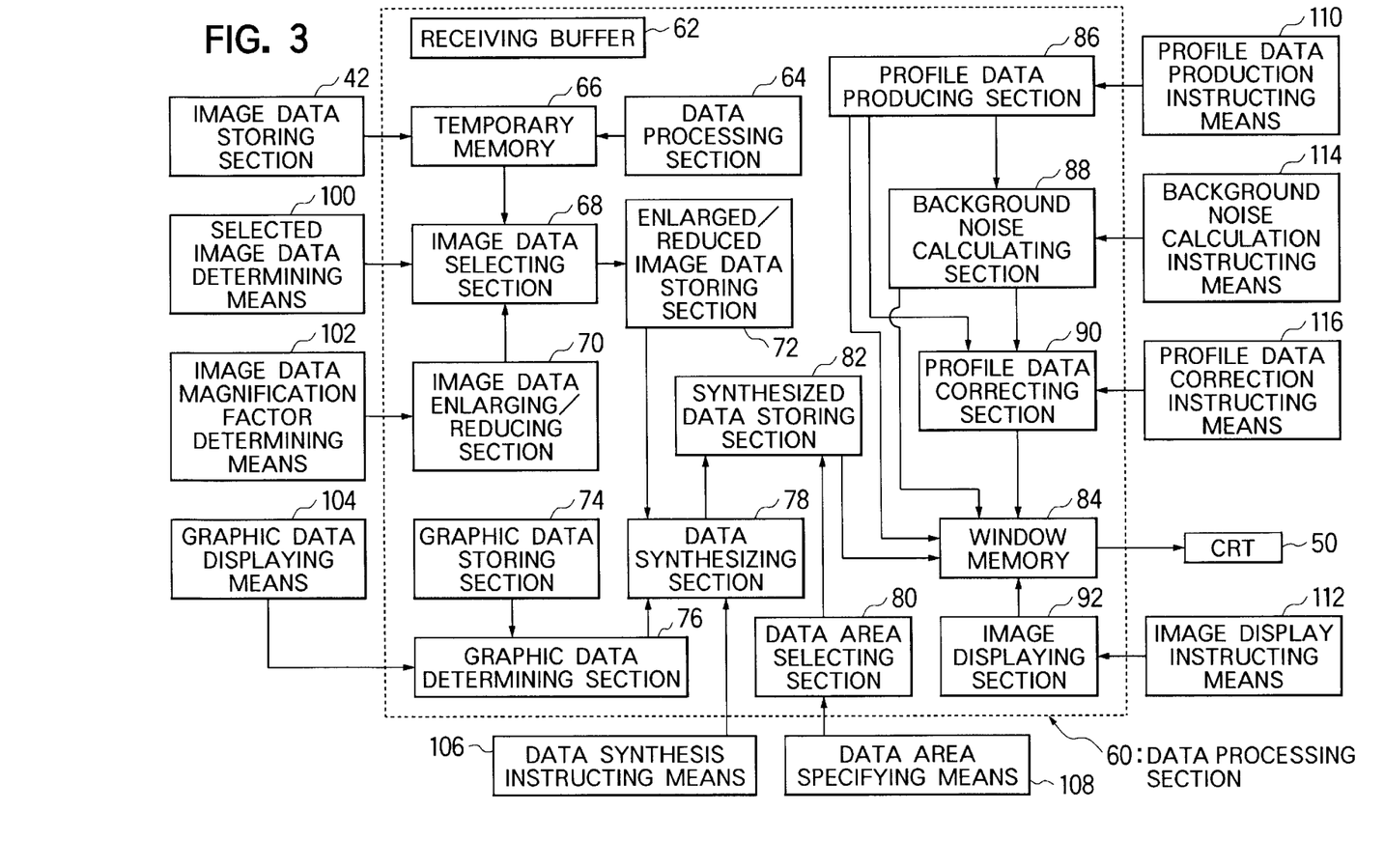
FIG. 3 is a block diagram of data processing means.

FIG. 3 is a block diagram of the data processing means 60.

As shown in FIG. 3, the data processing means 60 includes the receiving buffer 62 for receiving image data from the transmitting buffer 14 in the image reading apparatus 20, the data processing section 64 for effecting data processing and the temporary memory 66 for two-dimensionally mapping image data and temporarily storing them.

The data processing means 60 further includes an image data selecting section 68 for selecting a part of the image data from among the image data temporarily stored in the temporary memory 66, an image data enlarging/reducing section 70 for enlarging or reducing the image data selected by the image data selecting section 68, an enlarged/reduced image data storing section 72 for two-dimensionally mapping and temporarily storing the image data enlarged or reduced by the image data enlarging/reducing section 70, a graphic data storing section 74 for storing various graphic data to be displayed on the CRT 50, a graphic data determining section 76 for selecting predetermined graphic data from among the graphic data stored in the graphic data storing section 74 and specifying the position and the size of the graphic data in order to superpose them on the image data two-dimensionally mapped and temporarily stored in the enlarged/reduced image data storing section 72, a data synthesizing section 78 for synthesizing the image data temporarily stored in the enlarged/reduced image data storing section 72 and the graphic data selected by the graphic data determining section 76 and to be displayed on the CRT 50, a synthesized image data storing section 82 for two-dimensionally mapping and temporarily storing the image data and the graphic data synthesized by the data synthesizing section 78, a data area selecting section 80 for selecting a predetermined data area from among the image data and the graphic data temporarily stored in the synthesized image data storing section 82, a window memory 84 for two-dimensionally mapping and temporarily storing the data in the data area of the image data and graphic data selected by the data area selecting section 80, a profile data producing section 86 for producing density profile data of the image data surrounded by a predetermined figure generated in the window memory 84, which correspond to density of an image, and writing them in the window memory 84, background noise calculating section 88 for calculating background noise, a profile data correcting section 90 for correcting the density profile data written in the window memory 84 based on the background noise calculated by the background noise calculating section 88, and an image displaying section 92 for displaying an image based on the image data and the graphic data stored in the window memory 84 and profiles based on the profile data produced by the profile data producing section 86 and the profile data corrected by the profile data correcting section.

An image data selecting signal is input to the image data selecting section 68 from selected image data determining means 100, and an enlarging/reducing signal is input to the image data enlarging/reducing section 70 from image data magnification factor determining means 102. Further, a graphic data displaying signal is input to the graphic data determining section 76 from graphic data displaying means 104 and a data synthesizing signal is input to the data synthesizing section 78 from data synthesis instructing means 106 which determines what graphic data should be selected and how the image data and the graphic data are to be synthesized to be displayed on the CRT 50. Moreover, a data area specifying signal is input to the data area selecting section 80 from data area specifying means 108 and a profile data producing signal is input to the profile data producing section 86 from profile data production instructing means 110. Further, an image display instructing signal is input to the image displaying section 92 from image display instructing means 112 and background noise calculating signal is input to the background noise calculating section 88 from background noise calculation instructing means 114. A profile data correction instructing signal is input to the profile data correcting section 90 from profile data correction instructing means 116.

In this embodiment, the selected image data determining section 90, the image data magnification factor determining section 92, the graphic data displaying means 104, the data synthesis instructing means 106, the data area specifying means 108, the profile data production instructing means 110, the image display instructing means 112, the background noise calculation instructing means 114 and the profile data correction instructing means 116 can be operated by a mouse (not shown).

The thus constituted image analyzing apparatus which is an embodiment of the present invention displays a desired figure on the screen of the CRT 50 together with an image based on the image data stored in the image data storing means 40 and the graphic data stored in the graphic data storing section 74 in the following manner.

First, image data stored in the image data storing section 42 are two-dimensionally mapped and temporarily stored in the temporary memory 66. When the selected image data determining means 100 is operated, a part of the image data two-dimensionally mapped and stored in the temporary memory 66 is selected and two-dimensionally mapped and temporarily stored in the image data selecting section 68. The image data two-dimensionally mapped and stored in the image data selecting section 68 are then two-dimensionally mapped and stored in the enlarged/reduced image data storing section 72 without being enlarged or reduced and two-dimensionally mapped and stored in the synthesized image data storing section 82 without being synthesized with any graphic data. The image data two-dimensionally mapped and stored in the synthesized image data storing section 82 are two-dimensionally mapped and stored in the window memory 84 and an image is displayed on the screen of the CRT 50 based on the image data by operating the image display instructing means 112.

The operator views the image displayed on the screen of the CRT 50 and, as occasion demands, operates the image data magnification factor determining means 102, thereby enlarging or reducing the image data two-dimensionally mapped and stored in the image data selecting section 68 and two-dimensionally mapping and storing the image data in the enlarged/reduced image data storing section 72. The image data two-dimensionally mapped and stored in the enlarged/reduced image data storing section 72 are then read out by the data synthesizing section 78 to be two-dimensionally mapped and stored in the synthesized image data storing section 82. When the operator specifies a part of region of the image data two-dimensionally mapped and stored in the synthesized image data storing section 82 by operating the data area specifying means 108, the thus specified image data are forwarded into the window memory 84 and two-dimensionally mapped and stored therein. When the image display instructing means 112 is operated, an image is displayed on the screen of the CRT 50 by the image displaying section 92.

The autoradiographic image of the radioactively labeled substance in a gene generated using the Southern blot hybridization method includes a plurality of lanes and a plurality of spot image regions one-dimensionally distributed are formed in each lane. In this autoradiographic detecting process, it is often required to define an image region using a figure to produce a profile of density and analyze the image.

In the case where an image region in the image displayed on the screen of the CRT 50 is defined using a figure, the operator first uses the mouse to operate the data synthesis instructing means 106, thereby entering an instruction to synthesize the image data and graphic data. The operator manipulates the mouse to operate the image display instructing means 112 so that a desired image region is defined by a figure, while viewing the image displayed on the screen of the CRT 50. As a result, a graphic data displaying signal including positional information in accordance with the manipulation of the mouse is input to the graphic data determining section 76 and graphic data corresponding to the positional information are read out from the graphic data storing section 74 by the graphic data determining section 76 so that coordinate data of the graphic data in the image data, which correspond to a desired figure, are stored in the graphic data determining section 76. The graphic data are then read into the data synthesizing section 78 and synthesized with the image data two-dimensionally mapped and stored in the enlarged/reduced image data storing section 72. The thus synthesized image data and graphic data are two-dimensionally mapped and stored in the synthesized image data storing section 82 and forwarded to the window memory 84 so that a figure is displayed on the image displayed on the screen of the CRT 50 based on the graphic data.

When a density profile of an image region defined by the thus displayed figure is produced, the operator inputs a profile data producing signal to the profile data producing section 86 by operating the profile data production instructing means 110 and causes the profile data producing section 86 to sum up density levels of pixels contained in the image region defined by the figure, thereby producing density profile data. The thus produced density profile data are output to the window memory 84 and temporarily stored therein, whereafter a density profile is displayed on the screen of the CRT 50 based on the density profile data. As shown in FIG. 4, the thus displayed density profile normally contains background noise of a constant density level, since the stimulable phosphor sheet is uniformly exposed to ambient radiation or the like. Therefore, it is necessary to remove the background noise for obtaining a correct density profile.

Figure 5:
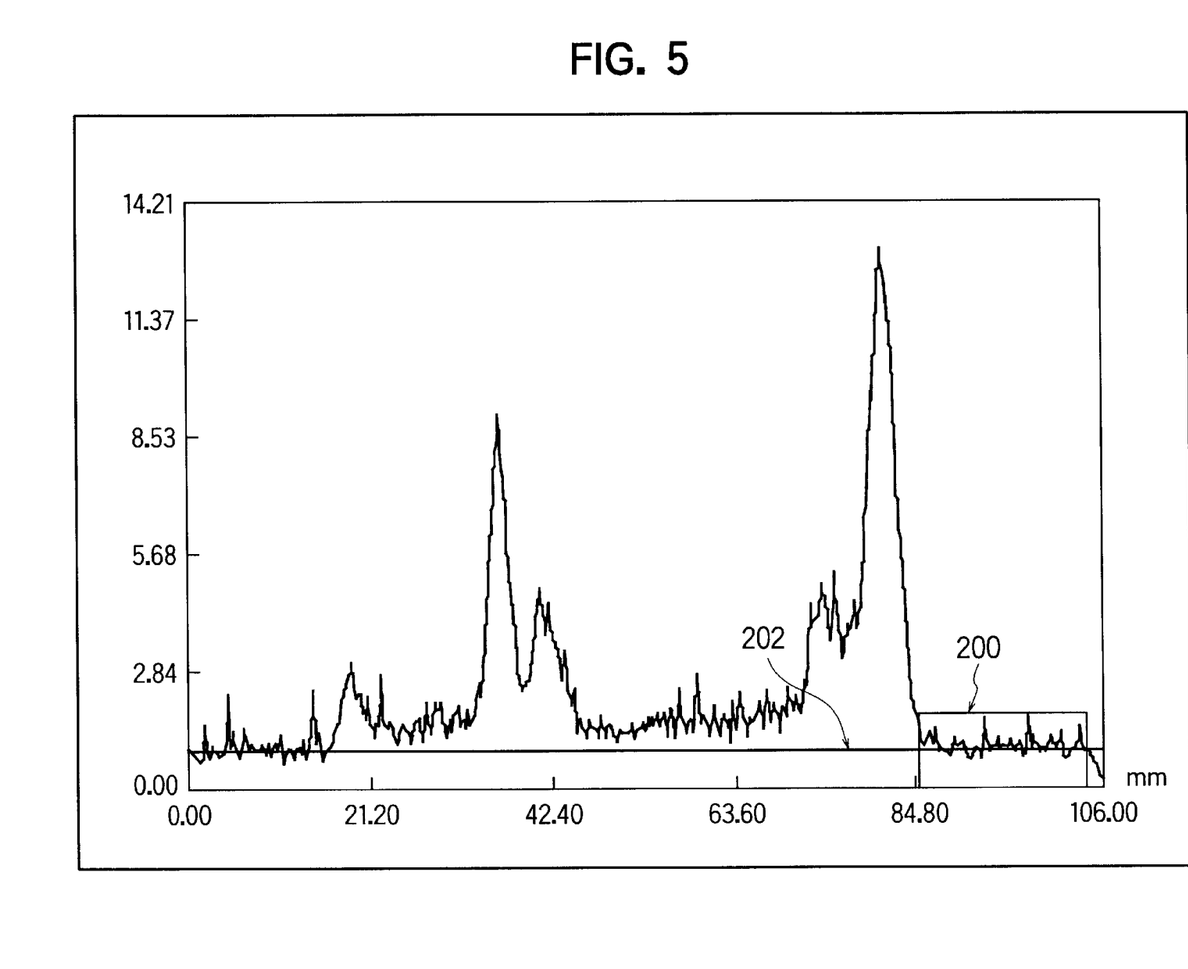
FIG. 5 shows a screen of CRT in which a region of interest is defined in a density profile and a density level of background noise is displayed.

In view of the above, according to this embodiment, the background noise calculating section 88 is constituted so as to calculate an average value of density levels in a region of interest specified by the operator in the density profile displayed on the screen of the CRT 50 and output it as the density level of background noise to the profile data correcting section 90 and the profile data correcting section 90 is constituted so as to subtract the density level of the background noise input from the background noise calculating section 88 from the profile data input from the profile data producing section 86 to correct the profile data and display the density profile on the screen of the CRT 50. More specifically, the operator manipulates the mouse to operate the background noise calculating section 88, while viewing the density profile displayed on the screen of the CRT 50 and defines a region of interest 200 in the density profile displayed on the screen of the CRT 50. When the region of interest has been defined, the background noise calculating section 88 calculates the average value of density levels of pixels contained in the region of interest 200 based on the image data corresponding to an image defined by the region of interest 200 among the image data two-dimensionally mapped and temporarily stored in the window memory 84 and outputs it as the density level of background noise to the window memory 84 and the profile data correcting section 90. The window memory 84 synthesizes the density level of the background noise input from the background noise calculating section 88 with the profile data input from the profile data producing section 86 and temporarily stored therein and displays the density profile on the screen of the CRT 50. FIG. 5 shows the density profile displayed on the screen of the CRT 50 based on the profile data thus synthesized with the density level 202 of the background noise calculated by the background noise calculating section 88. When the density level 202 of the background noise has been displayed on the screen of the CRT 50 together with the density profile in this manner, the operator judges based on his or her experience whether or not the density level 202 of the background noise displayed on the screen of the CRT 50 is acceptable. When the operator judges that the density level 202 of the background noise is unacceptable, he or she again manipulates the mouse to operate the background noise calculating section 88, while viewing the density profile displayed on the screen of the CRT 50 and defines another region of interest 200 in the density profile displayed on the screen of the CRT 50. The operator then causes the background noise calculating section 88 to calculate the density level of the background noise and the window memory to display the density level of the background noise on the screen of the CRT 50. These operations are repeated until an acceptable density level of the background noise is displayed on the screen of the CRT 50. To the contrary, when the operator judges that the density level 202 of the background noise is acceptable, he or she manipulates the mouse to operate the profile data correction instructing means 116 and inputs a profile data correction instructing signal to the profile data correcting section 90. When the profile data correcting section 90 receives the profile data correction instructing signal from the profile data correction instructing means 116, it reads out the profile data from the profile data producing section 86. The profile data correcting section 90 then subtracts the density level of the background noise input from the background noise calculating section 88 from the thus read out profile data to correct the profile data and outputs the corrected profile data to the window memory 84. The profile data corrected by the profile data correcting section 90 and output to the window memory 84 are temporarily stored in the window memory 84 and then displayed as a density profile on the screen of the CRT 50.

According to the above described embodiment, the operator views the density profile displayed on the screen of the CRT 50, defines a region of the density profile suitable for calculating the density level of the background as a region of interest, calculates the average value of density of pixels contained in the region of interest and corrects the density profile using the average value as the density level of the background. Therefore, it is possible to produce the density profile much more accurately than when correcting the density profile using the lowest value of density values as the density level of the background and markedly improve the accuracy of analyzing images. Further, even an unskilled operator can produce a correct density profile and analyze an image with high accuracy. Moreover, in this embodiment, since the density level of the background calculated by the background noise calculating section 88 is displayed on the screen of the CRT 50 together with the profile of density produced by the profile data producing section 86, the operator can judge whether or not an acceptable region of interest has been defined and determine an acceptable region of interest to remove the background noise from the profile data. Therefore, it is possible to improve the accuracy of analyzing images even more markedly.

The present invention has thus been shown and described with reference to a specific embodiment. However, it should be noted that the present invention is in no way limited to the details of the described arrangements but changes and modifications may be made without departing from the scope of the appended claims.

For example, in the above described embodiment, the explanation is made as to producing the density profile of the autoradiographic image of a radioactively labeled substance in a gene obtained using the Southern blot hybridization method. However, the present invention is not limited to such autoradiography and can also be applied for producing of a density profile of autoradiographic images such as an autoradiographic image of a protein produced by thin layer chromatography (TLC), an autoradiographic image produced by polyacrylamide gel electrophoresis for the separation or identification of a protein or the estimation of the molecular weight or properties of a protein, an autoradiographic image for studying the metabolism, absorption, excretion path and state of a substance introduced into a test animal such as a mouse or the like. Further, the present invention is applicable for producing a density profile of chemiluminescent images produced by a chemiluminescent process such as a chemiluminescent image of a gene produced by the Southern blot hybridization method, a chemiluminescent image of a protein produced by thin layer chromatography, a chemiluminescent image produced by polyacrylamide gel electrophoresis for the separation or identification of a protein or the estimation of the molecular weight or properties of a protein or the like. Moreover, the present invention can be widely applied for producing a density profile of an electron beam transmission image or an electron beam diffraction image of a metal or nonmetal produced by an electron microscope, an electron beam image of tissue of an organism and a radiographic diffraction image of a metal or nonmetal.

Further, in the above described embodiment, although the image data are produced by using the stimulable phosphor sheet 1 and converting locational information regarding a radioactive labeled substance to an electrical signal and are displayed on the CRT 50 as a visible image, it is possible to once form a visible image on a photographic film instead of the stimulable phosphor sheet 1, photoelectrically read the visible image, convert it to an electrical signal and process the thus obtained image data in a similar manner to the above.

Furthermore, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide an image analyzing apparatus which can produce a density profile of an image region in a gray image in a desired manner and analyze images.

What is claimed is:

1. An image analyzing apparatus, comprising:
    means for storing image data corresponding to an image comprising pixels,
    storing means for two-dimensionally mapping and temporarily storing at least a part of said image data stored in said image data storing means, and producing a density profile of a predetermined image region,
    a display for displaying at least one of an image based on said image data temporarily stored in said storing means and said density profile,
    means for producing density profile data of said density profile of said predetermined image region by summing density levels of said pixels corresponding to said predetermined image region, and storing said density profile data in said storing means,
    means for defining a region of interest in said density profile displayed on said display based on said density profile data and calculating an average value of density levels of said pixels corresponding to said region of interest as a background noise level, and
    means for subtracting said background noise level from said density profile data to correct said density profile data, and storing corrected density profile data in said storing means.

2. An image analyzing apparatus in accordance with claim 1, wherein said background noise level calculating means outputs said background noise level to said storing means, and wherein said display synthesizes said density profile data and said background noise level and displays synthesized data.

3. An image analyzing apparatus in accordance with claim 1, wherein said image data are produced using a stimulable phosphor sheet.

4. An image analyzing apparatus in accordance with claim 2, wherein said image data are produced using a stimulable phosphor sheet.

5. An image analyzing apparatus in accordance with claim 1, wherein said image data comprises image data selected from a group consisting of autoradiographic image data, radiographic diffraction image data, electron microscopic image data and chemiluminescent image data.

6. An image analyzing apparatus in accordance with claim 2, wherein said image data comprises image data selected from a group consisting of autoradiographic image data, radiographic diffraction image data, electron microscopic image data and chemiluminescent image data.

7. An image analyzing apparatus in accordance with claim 3, wherein said image data comprises image data selected from a group consisting of autoradiographic image data, radiographic diffraction image data, electron microscopic image data and chemiluminescent image data.

8. An image analyzing apparatus in accordance with claim 4, wherein said image data comprises image data selected from a group consisting of autoradiographic image data, radiographic diffraction image data, electron microscopic image data and chemiluminescent image data.

9. An image analyzing apparatus in accordance with claim 5, wherein said autoradiographic image data, said radiographic diffraction image data and said electron microscopic image data are produced by absorbing and storing the energy of a radiation or an electron beam emitted from a specimen stored in a stimulable phosphor, irradiating the stimulable phosphor with an electromagnetic wave and photoelectrically converting light emitted from the stimulable phosphor.

10. An image analyzing apparatus in accordance with claim 6, wherein said autoradiographic image data, said radiographic diffraction image data and said electron microscopic image data are produced by absorbing and storing the energy of a radiation or an electron beam emitted from a specimen stored in a stimulable phosphor, irradiating the stimulable phosphor with an electromagnetic wave and photoelectrically converting light emitted from the stimulable phosphor.

11. An image analyzing apparatus in accordance with claim 7, wherein said autoradiographic image data, said radiographic diffraction image data and said electron microscopic image data are produced by absorbing and storing the energy of a radiation or an electron beam emitted from a specimen stored in a stimulable phosphor, irradiating the stimulable phosphor with an electromagnetic wave and photoelectrically converting light emitted from the stimulable phosphor.

12. An image analyzing apparatus in accordance with claim 8, wherein said autoradiographic image data, said radiographic diffraction image data and said electron microscopic image data are produced by absorbing and storing the energy of a radiation or an electron beam emitted from a specimen stored in a stimulable phosphor, irradiating the stimulable phosphor with an electromagnetic wave and photoelectrically converting light emitted from the stimulable phosphor.

13. An image analyzing apparatus in accordance with claim 5, wherein said chemiluminescent image data are produced by absorbing and storing the energy of a visible light emitted from a specimen stored in a stimulable phosphor, irradiating the stimulable phosphor with an electromagnetic wave and photoelectrically converting light emitted from the stimulable phosphor.

14. An image analyzing apparatus in accordance with claim 6, wherein said chemiluminescent image data are produced by absorbing and storing the energy of a visible light emitted from a specimen stored in a stimulable phosphor, irradiating the stimulable phosphor with an electromagnetic wave and photoelectrically converting light emitted from the stimulable phosphor.

15. An image analyzing apparatus in accordance with claim 7, wherein said chemiluminescent image data are produced by absorbing and storing the energy of a visible light emitted from a specimen stored in a stimulable phosphor, irradiating the stimulable phosphor with an electromagnetic wave and photoelectrically converting light emitted from the stimulable phosphor.

16. An image analyzing apparatus in accordance with claim 8, wherein said chemiluminescent image data are produced by absorbing and storing the energy of a visible light emitted from a specimen stored in a stimulable phosphor, irradiating the stimulable phosphor with an electromagnetic wave and photoelectrically converting light emitted from the stimulable phosphor.

17. An image analyzing apparatus according to claim 1, wherein said means for producing density profile data comprises:

a profile data production instructing unit.

18. An image analyzing apparatus according to claim 1, wherein said means for calculating said average value of density levels of said pixels corresponding to said region of interest as a background noise level comprises:

a background noise calculating instruction unit for receiving a background noise level instruction from a user and outputting an instruction signal; and a background noise calculating section which calculates said average value in response to said instructions signal.

19. An image analyzing apparatus according to claim 1, wherein said means for subtracting said background noise from said density profile data comprises:

a profile data correction instruction unit for receiving a profile data correction instruction from a user and outputting an instruction signal; and a profile data correcting section which produces said corrected density profile data in response to said instructions signal.

20. An image analyzing apparatus, comprising:

an image data storage unit for storing image data corresponding to an image comprising pixels;

a memory for two-dimensionally mapping and temporarily storing at least a part of said image data;

an image data selecting unit for selecting and storing a portion of said at least part of said image data as selected image data;

a graphic data storing unit for storing graphic data;

a graphic data determining unit for selecting specific graphic data from graphic data stored in said graphic data storing unit;

a data synthesizing unit for receiving said selected image data from said image data selecting unit and said specific graphic data from said graphic data determining unit, and synthesizing said selected image data and said specific graphic data to output synthesized data;

a data synthesizing storing unit for storing said synthesized data;

a data area selecting unit for selecting a region of said synthesized data;

a window memory for receiving and storing said region of said synthesized data;

a profile data unit for producing density profile data of said region of said synthesized data by summing density levels of said pixels corresponding to said region;

a background noise calculating unit for calculating an average value of density levels of said pixels in said region and outputting said average value as a background noise level; and a profile data correcting unit for calculating said corrected density profile data by subtracting said background noise level supplied from said background noise level calculating unit from said density profile data supplied from said profile data unit.

21. An image analyzing apparatus according to claim 20, further comprising:

a selected image data input unit for outputting an image data selecting signal to said image data selecting unit, in response to input from a user, for selecting said selected image data;

a graphic data input unit for outputting a graphic data displaying signal to said graphic data determining unit, in response to input from the user, to output said specific graphic data;

a data synthesis input unit for outputting a data synthesizing signal to said data synthesizing unit, in response to input from the user, for controlling synthesis of said selected image data and said specific graphic data; and a data area selecting unit for outputting a data area specifying signal to said synthesized data storing unit, in response to input from the user, for selecting said region of said synthesized data.

22. An image analyzing apparatus, comprising:

an image data storage unit for storing image data corresponding to an image comprising pixels;

a memory for two-dimensionally mapping and temporarily storing at least a part of said image data;

an image data selecting unit for selecting and storing a portion of said at least part of said image data as selected image data;

a data area selecting unit for selecting a region of said selected image data;

a window memory for receiving and storing said region of said selected image data;

a profile data unit for producing density profile data of said region stored in said window memory by summing density levels of said pixels corresponding to said region;

a background noise calculating unit for calculating an average value of density levels of said pixels in said region stored in said window memory and outputting said average value as a background noise level; and a profile data correcting unit for receiving said background noise level and calculating said corrected density profile data by subtracting said background noise level supplied from said background noise level calculating unit from said density profile data supplied from said profile data unit.

* * * * *